United States Patent
Ou et al.

(10) Patent No.: US 7,902,414 B2
(45) Date of Patent: Mar. 8, 2011

(54) PARA-XYLENE PRODUCTION PROCESS EMPLOYING IN-SITU CATALYST SELECTIVATION

(75) Inventors: John D. Y. Ou, Houston, TX (US);
Zongxuan Hong, Houston, TX (US);
Songsheng Tan, Sugarland, TX (US);
Timothy E. McMinn, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 51 days.

(21) Appl. No.: 11/866,847

(22) Filed: Oct. 3, 2007

(65) Prior Publication Data
US 2008/0033067 A1 Feb. 7, 2008

Related U.S. Application Data

(62) Division of application No. 10/294,427, filed on Nov. 14, 2002, now abandoned.

(51) Int. Cl.
*C07C 2/66* (2006.01)
*C07C 2/86* (2006.01)
(52) U.S. Cl. ......... 585/446; 585/454; 585/467; 585/469; 585/448; 585/470; 585/471; 585/805
(58) Field of Classification Search .................. 585/446, 585/448, 470, 471, 805, 454, 467, 469
See application file for complete search history.

(56) References Cited

U.S. PATENT DOCUMENTS

| | | | |
|---|---|---|---|
| 3,965,207 A | 6/1976 | Weinstein | |
| 4,001,346 A | 1/1977 | Chu | |
| 4,002,698 A | 1/1977 | Kaeding | |
| 4,128,592 A | 12/1978 | Kaeding | |
| 4,354,963 A | 10/1982 | Butter et al. | |
| 4,477,585 A | 10/1984 | Kaeding | |
| 4,487,984 A | 12/1984 | Imai | |
| 4,617,035 A | 10/1986 | Wakaizumi et al. | |
| 4,665,238 A | 5/1987 | Imai et al. | |
| 5,173,461 A | 12/1992 | Absil et al. | |
| 5,271,920 A | 12/1993 | Chang et al. | |
| 5,382,737 A * | 1/1995 | Beck et al. | 585/475 |
| 5,475,179 A | 12/1995 | Chang et al. | |
| 5,625,103 A | 4/1997 | Abichandani et al. | |
| 6,048,816 A * | 4/2000 | Brown et al. | 502/77 |
| 6,187,982 B1 * | 2/2001 | Beck et al. | 585/409 |
| 6,388,156 B1 | 5/2002 | Ou et al. | |
| 6,459,006 B1 | 10/2002 | Ou et al. | |
| 7,326,818 B2 * | 2/2008 | Beeckman et al. | 585/475 |
| 2003/0004383 A1 * | 1/2003 | Brown et al. | 585/467 |

FOREIGN PATENT DOCUMENTS

| | | |
|---|---|---|
| JP | 59216837 | 12/1984 |
| JP | 61221137 | 10/1986 |
| RU | 2 119 470 C | 9/1998 |
| WO | 96/15083 | 5/1996 |
| WO | 97/46636 | 12/1997 |
| WO | 98/14415 | 4/1998 |
| WO | 00/69796 | 11/2000 |
| WO | 00/74847 | 12/2000 |
| WO | 01/32591 | 5/2001 |

OTHER PUBLICATIONS

Cejka et al., "Decisive role of transport rate of products for zeolite para-selectivity: Effect of coke deposition and external surface silylation on activity and selectivity of HZSM-5 in alkylation of toluene", Zeolites 17: 1996, pp. 265-271.
Sotelo et al., "Deactivation Kinetics of Toluene Alkylation with Methanol over Magnesium-Modified ZSM-5", Ind. Eng. Chem. Res., 1996, 35, pp. 1300-1306.
Prakash et al., "Synthesis and Characterization of the Large-pore Molecular Sieve SAPO-46", J. Chem. Soc. Faraday Trans., 1995, 91(6), pp. 1045-1050.
Sotelo et al., "Deactivation of toluene alkylation with methanol over magnesium-modified ZSM-5 Shape selectivity changes induced coke formation", Applied Catalysis A: General 114 (1994), pp. 273-285.
Kulkarni et al., "The correlation between sorption and catalytic properties of HZSM-5 type catalysts", Applied Catalysis, 8 (1983), pp. 43-56.
Kaeding et al., "Selective alkylation of Toluene with Methanol to Produce para-Xylene", Journal of Catalysis, 67, 1981, pp. 159-174.
Ashton et al., "The Catalytic Properties of Modified Pentasil Zeolites", Journal of Molecular Catalysis, 34 (1986), pp. 73-83.

* cited by examiner

*Primary Examiner* — Elizabeth D Wood
(74) *Attorney, Agent, or Firm* — Andrew B. Griffis

(57) ABSTRACT

A catalytic process for the selective production of para-xylene comprises the step of reacting an aromatic hydrocarbon selected from the group consisting of toluene, benzene and mixtures thereof with a feed comprising carbon monoxide and hydrogen in the presence of a selectivated catalyst. The process includes a catalyst selectivation phase and a para-xylene production phase. In the catalyst selectivation phase, the aromatic hydrocarbon and the feed are contacted with the catalyst under a first set of conditions effective to increase the para-selectivity of said catalyst. In the para-xylene production phase, the aromatic hydrocarbon and said feed are contacted with the catalyst under a second set of conditions different from the first set of conditions effective to selectively produce para-xylene.

12 Claims, No Drawings

PARA-XYLENE PRODUCTION PROCESS EMPLOYING IN-SITU CATALYST SELECTIVATION

This application is a divisional of U.S. patent application Ser. No. 10/294,427, filed Nov. 14, 2002, and now abandoned the entirety of which is incorporated by reference.

FIELD

This invention relates to a process for producing para-xylene which employs in-situ catalyst selectivation and to a selectivated catalyst for use in the process.

BACKGROUND

Of the xylene isomers, i.e., ortho-, meta- and para-xylene, para-xylene (PX) is of particular value as a large volume chemical intermediate in a number of applications such as the manufacture of terephthalates, which are intermediates for the manufacture of PET. One source of feedstocks for manufacturing PX is the disproportionation of toluene into xylenes. A disadvantage of this process is that large quantities of benzene are also produced. Another source of feedstocks used to obtain PX involves the isomerization of a feedstream that contains non-equilibrium quantities of mixed ortho- and meta-xylene isomers (OX and MX, respectively) and is lean with respect to PX content. A disadvantage of this process is that the separation of the PX from the other xylene isomers is expensive.

An alternative process for the production of xylenes is by the methylation of toluene using a zeolite or other catalyst composition. For instance, U.S. Pat. No. 3,965,207 discloses the methylation of toluene with methanol using a zeolite catalyst such as a ZSM-5. However, existing toluene methylation processes suffer from the disadvantage that the catalyst tends to deactivate rapidly due to build up of coke and heavy by-products. In addition, the methanol selectivity to para-xylene, the desirable product, has been low, typically in the range of 50 to 60%.

It is also known that alkylaromatic compounds can be synthesized by reacting an aromatic compound, such as toluene, with a mixture of carbon monoxide (CO) and hydrogen ($H_2$) (syngas) at alkylation conditions in the presence of a catalyst system, which comprises (1) a composite of the oxides of zinc, copper, chromium, and/or cadmium; and (2) an aluminosilicate material, either crystalline or amorphous, such as zeolites or clays. See, for example, U.S. Pat. Nos. 4,487,984 and 4,665,238. Such catalyst systems are, however, subject to rapid deactivation and are not capable of producing greater than equilibrium concentrations of para-xylene (PX) in the xylene-fraction product. Typically, the xylene-fraction product contains a mixture of xylene isomers at or near the equilibrium concentration, i.e., 24% PX, 54% MX, and 22% OX. The lack of para-xylene selectivity in alkylation of toluene with syngas can be caused by (1) the presence of acidic sites on the surface of the zeolite, and/or (2) the channel structure of the zeolite not being able to differentiate para-xylene from its isomers.

It is also known that in-situ catalyst-selectivation can increase the selective production of para-xylene. For example, U.S. Pat. No. 5,475,179, which is incorporated herein by reference, teaches a process for selectively producing para-xylene disproportionation of toluene in the presence of a zeolite catalyst that has undergone in-situ silicon selectivation. The selectivation requires adding a silicon selectivating agent to the disproportionation feed and subsequently removing the selectivating agent from the feed when the reaction is switched to a normal production stage. Such processes produce high para-xylene selectivity, but have reduced catalyst activity. Further, the selectivation cannot be performed without switching of the feeds to the reaction. This complicates the selectivation process and requires that certain feeds involved in the selectivation need to be shutdown for the process to be returned to normal production.

U.S. Pat. No. 5,625,103, which is incorporated herein by reference, teaches a continuous toluene disproportionation process which employs both ex-situ silicon selectivation and in-situ coke selectivation. In this process, a silicon-selectivated ZSM-5 catalyst is contacted with a toluene feed for an initial, high temperature adjustment phase, where coke is deposited on the catalyst to enhance its para-selectivity, and for a subsequent steady-state phase, where the toluene is selectively converted to para-xylene.

The present invention seeks to provide a catalyst and process for producing para-xylene by the selective alkylation of benzene and/or toluene with syngas in which a high degree of selectivity can be achieved without diminishing catalyst activity and without addition of separate selectivating agents.

SUMMARY

In one aspect, the invention resides in a catalyst useful in the selective production of para-xylene, the catalyst comprising a molecular sieve and having been treated with carbon monoxide at conditions effective to decrease the diffusivity of the catalyst such that the catalyst has a Diffusion Parameter, $D/r^2$, for 2,2-dimethylbutane of less than 100, such as less than 5, when measured at a temperature of 120° C. and a 2,2-dimethylbutane relative pressure of 0.013.

Conveniently, the catalyst has a Diffusion Parameter, $D/r^2$, for 2,3-dimethylbutane of less than 1000, such as less than 600, when measured at a temperature of 120° C. and a 2,3-dimethylbutane relative pressure of 0.012.

Conveniently, the catalyst has been treated with carbon monoxide and hydrogen or with carbon monoxide, hydrogen and toluene.

In a further aspect, the invention resides in a process for the selective production of para-xylene comprising the steps of reacting an aromatic hydrocarbon selected from toluene, benzene and mixtures thereof with a feed comprising carbon monoxide and hydrogen in the presence of the catalyst of said one aspect of the invention.

In yet a further aspect, the invention resides in a process for the selective production of para-xylene comprising the steps of reacting an aromatic hydrocarbon selected from toluene, benzene and mixtures thereof with a feed comprising carbon monoxide and hydrogen in the presence of a catalyst, wherein the process includes a catalyst selectivation phase and a para-xylene production phase and wherein:

(a) said catalyst selectivation phase includes the step of contacting said aromatic hydrocarbon and said feed with said catalyst under a first set of conditions effective to increase the para-selectivity of said catalyst, and (a) said para-xylene production phase includes the step of contacting said aromatic hydrocarbon and said feed with said catalyst under a second set of conditions different from said first set of conditions and effective to selectively produce para-xylene.

The difference between said second set of conditions and said first set of conditions may reside in the molar concentration and/or feed rate of any one of said aromatic hydrocarbon, carbon monoxide and hydrogen, the reaction temperature and/or the reaction pressure.

Conveniently, the selectivation phase occurs before the production phase.

Alternatively, the selectivation phase interrupts the production phase, which resumes once the selectivation phase is completed.

Conveniently, the temperature of the selectivation phase greater than that of the production phase.

Conveniently, the temperature of the selectivation phase is between 100 and 700° C., preferably between 200 and 600° C.

Conveniently, the pressure of the selectivation phase is between 1 and 300 atm, preferably between 1 and 200 atm.

Conveniently, the hydrocarbon stream has a flow rate during the selectivation phase between 0.01 and 100 $h^{-1}$ WHSV, preferably between 1 and 50 $h^{-1}$ WHSV.

Conveniently, the molar ratio of $H_2$/CO/aromatic hydrocarbon is 0.01-10/0.01-10/0.01-10 respectively.

In still a further aspect, the invention resides in a process for the selectivation of a catalyst composition for the synthesis of para-xylene in a continuous reaction having a selectivation phase and a production phase comprising:
(i) feeding into a reactor a hydrocarbon stream comprising at least one of toluene, benzene and a mixture thereof;
(ii) feeding a gas stream comprising carbon monoxide and hydrogen into said reactor; and
(iii) contacting said hydrocarbon stream and said gas stream in said reactor in the presence of said catalyst composition;
wherein selectivation of said catalyst composition includes the step of altering for a limited period of time at least one of the molar concentration of said hydrocarbon stream in said reactor, the molar concentration of said gas stream in said reactor, the flow rate of said hydrocarbon stream, and the flow rate of said gas stream, the temperature in the reactor, and the pressure in the reactor; whereby the selectivation of said catalyst composition does not involve interruption of the feeding of said streams and further does not involve the addition of a selectivating agent different from said hydrocarbon stream and said gas stream.

DETAILED DESCRIPTION OF THE PREFERRED EMBODIMENTS

The present invention provides a catalyst and process for selectively producing para-xylene by contacting a hydrocarbon stream comprising toluene, benzene, or mixture thereof, with a gas stream comprising carbon monoxide and hydrogen in the presence of a catalyst composition. The process involves a catalyst selectivation phase conducted under a first set of conditions effective to increase the para-selectivity of said catalyst and a para-xylene production phase conducted under a second, different set of conditions effective to selectively produce para-xylene.

The catalyst composition employed in the process of the invention preferably includes (1) a first acidic component typically selected from one or more than one silicate-based materials, including but not necessarily limited to, crystalline or amorphous aluminosilicates, substituted aluminosilicates, substituted silicates, zeolite-bound zeolites, and/or crystalline or amorphous aluminophosphates, and/or substituted aluminophosphates and mixtures thereof, and, optionally (2) a second component of one or more than one of the metals or oxides of the metals selected from Groups 1, 2, 3, 4, 5, 6, 7, 8, 9, 10, 11, 12, 13, 14, 15, and 16 (new IUPAC notation). The weight ratio of the first acidic component to the metal or metal oxide second component, if present, may range from 100:1 to 1:100.

Suitable silicate-based materials for use as the first component of the catalyst composition of the invention include zeolites, particularly those having a Constraint Index of 1-12 (see U.S. Pat. No. 4,016,218, incorporated herein by reference). Examples of zeolites having a Constraint Index of 1-12 include ZSM-5, ZSM-11, ZSM-12, ZSM-22, ZSM-23, ZSM-35, ZSM-48, and MCM-22, with ZSM-5 and ZSM-11 being particularly preferred.

Zeolite ZSM-5 and the conventional preparation thereof are described in U.S. Pat. No. 3,702,886, the disclosure of which is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. ZSM-48 and the conventional preparation thereof is taught by U.S. Pat. No. 4,375,573, the disclosure of which is incorporated herein by reference. MCM-22 is disclosed in U.S. Pat. No. 4,954,325, the disclosure of which is incorporated by reference.

Other silicate-based materials suitable for the first component of the catalyst composition include zeolite bound zeolites as described in WO 97/45387, incorporated herein by reference. Zeolite bound zeolite catalysts useful in the present invention concern first crystals of an acidic intermediate pore size first zeolite and a binder comprising second crystals of a second zeolite. Unlike zeolites bound with amorphous material such as silica or alumina to enhance the mechanical strength of the zeolite, the zeolite bound zeolite catalyst suitable for use in the present process does not contain significant amounts of non-zeolitic binders.

Aluminophosphate-based materials may be used in conjunction with metal oxides for aromatic alkylation with syngas in accordance with the invention. Aluminophosphate-based materials usually have lower acidity compared to silicate-based materials. The lower acidity eliminates many side reactions, raises reactants' utilization, and extends catalyst life. Aluminophosphate-based materials are made of alternating $AlO_4$ and $PO_4$ tetrahedra. Members of this family have 8-(e.g. $AlPO_4$-12, -17, -21, -25, -34, -42, etc.), 10-(e.g. $AlPO_4$-11, 41, etc.), or 12-($AlPO_4$-5, -31, etc.) membered oxygen ring channels. Although $AlPO_4$s are neutral, substitution of Al and/or P by cations with lower charge introduces a negative charge in the framework, which is countered by cations imparting acidity.

For example, substitution of silicon for P and/or a P-Al pair turns the neutral binary composition (i.e. Al, P) into a series of acidic-ternary-composition (Si, Al, P) based SAPO materials, such as SAPO-5, -11, -14, -17, -18, -20, -31,-34, -41 and -46. Acidic ternary compositions can also be created by substituting divalent metal ions for aluminum, generating the MeAPO materials, where Me is a metal ion selected from Mg, Co, Fe, Zn and the like. Substitution can also create acidic quaternary compositions such as the MeAPSO series, including FeAPSO (Fe, Al, P, and Si), MgAPSO, MnAPSO, CoAPSO and ZNAPSO. Other substituted aluminophosphate-based materials include ElAPO and ElAPSO (where El=B, As, Be, Ga, Ge, Li, Ti, etc.). As mentioned above, these materials have the appropriate acidic strength for syngas/aromatic alkylation. The more preferred aluminophosphate-based materials for use in this invention include 10- and 12-membered ring materials (SAPO-11, -31, -41; MeAPO-11, -31, -41; MeAPSO-11, -31, 41; ElAPO-11, -31, -41; ElAPSO-11, -31, -41, etc.) which have significant shape selectivity due to their narrow channel structure.

Where the acidic first component of the catalyst composition is a molecular sieve, such as a zeolite, it may be desirable to subject the material to an initial ex-situ selectivation treatment so as to reduce the amount of selectivition required to achieve the desired diffucivity in the subsequent in-situ selectivation step. Ex-situ selectivation typically involves the treatment of the catalytic material with proper chemical compounds of elements selected from Groups 1-16, and mixtures thereof. The composition of the selectivated catalyst may range from 1 wt. % of the selectivating elements/99 wt. % of the first component to 99 wt. % of the selectivating elements/1 wt. % of the first component. By "selectivating elements" it is meant the elemental portion of the elemental form or elemental oxide form of the selectivating chemical compounds. Some para-selectivation treatments are known, e.g. using silicon compounds (see U.S. Pat. No. 5,476,823, incorporated herein by reference). Other compounds that may be used include, but are not limited to compounds of phosphorus, boron, antimony, magnesium, and the like, and coke, and the like.

The second component of the catalyst composition used in the process of the invention is one or more catalytically active metals or oxides of the metal elements selected from Groups 1, 2, 3 4, 5, 6, 7, 8, 9, 10, 11, 12, 13, 14, 15 and 16 (new IUPAC notation), wherein the metal is preferably zinc, copper, chromium, cadmium, palladium, ruthenium or manganese. The loading of the metal/metal oxide is preferably at least about 0.1 wt. %, and generally not more than 50 wt. %, preferably between 5 wt. % to 40 wt. %, of the total catalyst composition.

In one practical embodiment, the catalyst comprises ZSM-5 as the first component and oxides of zinc and copper as the second component.

The catalyst may also include a third inorganic oxide matrix component in the form of a binder, filler, and/or support for the catalyst. For example, the first and second components of the catalyst may be chemically combined and/or physically mixed and then the third inorganic oxide matrix component may be added for the purpose of binding the first and the second components together so that catalyst is hard enough to survive interparticle and reactor wall collisions.

The third component of catalyst composition may be made according to conventional methods from an inorganic oxide sol or gel, which is dried to "glue" the other components of the catalyst together. Preferably, the inorganic oxide matrix is not catalytically active and comprises oxides of silicon, aluminum, titanium, zirconium, and mixtures thereof. It is also preferred that separate alumina phases be incorporated into the inorganic oxide matrix. Species of aluminum oxyhydroxides-γ-alumina, boehmite, diaspore, and transitional aluminas such as α-alumina, β-alumina, γ-alumina, δ-alumina, ε-alumina, κ-alumina, and ρ-alumina can be employed. Preferably, the alumina species is an aluminum trihydroxide such as gibbsite, bayerite, nordstrandite, or doyelite. The matrix material may also contain phosphorous or aluminum phosphate. The matrix material may also contain clays such as kaolinite, bentonite, attapulgite, montmorillonite, clarit, fuller's earth, diatomaceous earth, and mixture thereof. The weight ratio of the combination of the solid acid component and the metal-based component to the inorganic oxide matrix component can be about 100:1 to 1:100.

Preparation of the catalyst composition can be accomplished by several techniques known to those skilled in the art, such as physical mixing, impregnation or co-precipitation. Some examples are given below.

For example, the catalyst composition can be prepared by adding solutions of metal salts either in series to or as a mixture with particles, such as extrudates, spheres, etc., of the first catalyst component until incipient wetness is reached. The solvent can be then evacuated under heat or vacuum using, for example, a rotary evaporator. The final product is then dried, calcined, and, if necessary, pelletized. Alternatively, finely divided powders of the first component and the metal(s) or metal oxide(s) can be physically mixed using a blending machine or a grinding mortar.

The catalyst composition system can also be formed by packing the first and the second components in a stacked-bed manner with some of the second component in front of the physical or chemical mixture of the first and second components.

Prior to use in the process of the invention, the catalyst composition can optionally be activated under a reducing environment (e.g. pure $H_2$ or diluted $H_2$ such as 1-80% $H_2$ in $N_2$) at 100-700° C., and 1-200 atm ($1.01 \times 10^5$-$2.03 \times 10^7$ Pa) for 2-48 hours.

The methylation process can be carried out as a continuous operation utilizing a fixed, moving bed, or CSTR catalytic reaction system, with or without recycle. Multiple injection of the methylating agent may be employed. The methylating agent includes syngas (CO and $H_2$) optionally together with $CO_2$ and/or $CH_3OH$ and derivatives thereof. In one preferred embodiment of the invention, methanol as the methylating agent is not separately added but is formed in situ.

Toluene and/or benzene and the methylating agent(s) are usually premixed and fed together into the reaction vessel to maintain the desired ratio between them with no local concentration of either reactant to disrupt reaction kinetics. Individual feeds can be employed, however, if care is taken to insure good mixing of the reactant vapors in the reaction vessel. Optionally, instantaneous concentration of methylating agent can be kept low by staged additions thereof. By staged additions, the ratios of toluene and/or benzene to methylating agent concentrations can be maintained at optimum levels to give good aromatic compound conversions and better catalytic reaction system stability.

The toluene can be pure, or in a mixture with benzene. The benzene may alkylate to toluene, and/or ultimately to PX, with or without recycle. The presence of benzene may also enhance heat and/or selectivity control.

The process of this invention is expected to tolerate many different kinds of feed. For example, premium extracted toluene, essentially pure toluene, and extracted aromatics, essentially a relatively pure mixture of toluene and benzene, may also be used. Unextracted toluene and/or benzene, which contain toluene, benzene, and olefins and paraffins that boil in a similar range to that of toluene or benzene, may also be employed. When unextracted feedstocks are used, it is important to crack the paraffins and olefins into lighter products that can be easily distilled. For example, the feed may contain one or more paraffins and/or olefins having at least 4 carbon atoms. However, the catalyst composition used in the process of the invention has the dual function of cracking paraffins and/or olefins and methylating benzene or toluene to selectively produce PX.

The reaction can be carried out at conditions known in the prior art. An example of such conditions is a reactor temperature that can range from about 100 to 700° C., preferably from about 200 to 600° C. Reactor pressure can be from about 1 to 300 atm, preferably from about 1 to 200 atm. Flow rate for the hydrocarbon feed can be from about 0.01 to 100 $h^{-1}$ WHSV, preferably from about 1 to 50 h$^{-1}$ WHSV on a liquid feed basis. The composition of the feed streams, i.e. the mole ratio of H$_2$/CO/aromatic compounds, can be about 0.01-10/0.01-10/0.01-10.

The process of the present invention includes an in-situ selectivation phase, during which the para-selectivity of the catalyst composition is enhanced, and a para-xylene production phase, where normal production of para-xylene is effected. The in-situ selectivation technique of the present invention is quite flexible and can be done either prior to para-xylene production phase or during the para-xylene production phase, by temporarily interrupting the para-xylene production phase. In either case, the selectivation involves altering the conditions of the reaction without actually changing the feeds or adding a selectivating agent. The conditions which can be altered include the molar ratios of the feeds, the temperature, pressure, and flow rates of the feeds. After selectivation is completed, the reaction conditions are then adjusted to desired levels for optimal para-xylene production. The conditions may be altered singularly, in combination or collectively as desired. Typically, the temperatures employed during selectivation is higher than the temperature used in the production phase.

A selectivation that is performed prior to a para-xylene production phase would, by way of example, proceed as follows:

(i) Dry the catalyst composition with an inert gas in the temperature range of 200-600° C.

(ii) Discontinue inert gas and set the reactor to the desired selectivation conditions, including appropriate molar compositions for the feeds of aromatic hydrocarbons and methylating gas mixtures.

(iii) In-situ selectivation, in which the catalyst increases para-xylene selectivity, is realized as production proceeds.

(iv) As the reaction continues to proceed, additional reaction conditions may be altered to further improve selectivation.

(v) As selectivation is maximized, the reaction conditions are altered to desired para-xylene production The in-situ selectivation process of the invention increases the diffusional resistance of the catalyst. Diffusional resistance for porous crystalline materials is typically reported as the Diffusion Parameter, $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

Where the catalyst employed in the present process comprises a molecular sieve as the first acidic component, the selectivation may be conducted such that the Diffusion Parameter, $D/r^2$, of the catalyst for 2,2-dimethylbutane is less than 100, such as less than 5, when measured at a temperature of 120° C. and a 2,2-dimethylbutane relative pressure at 120° C. of 0.013. Typically, the selectivated catalyst will also have a Diffusion Parameter, $D/r^2$, for 2,3-dimethylbutane of less than 1000, such as less than 600, when measured at a temperature of 120° C. and a 2,3-dimethylbutane relative pressure at 120° C. of 0.012.

The process of this invention is capable of producing mixtures of xylenes where PX comprises at least 30 wt. % of the mixture, preferably at least 36 wt. %, and most preferably at least 48 wt. %. The process of this invention is also capable of converting at least 5 wt. % of the aromatic compound to a mixture of xylenes, preferably greater than 15 wt. %.

Para-xylene may be recovered from the process stream, for example by crystallization, for use in products such as terephthalic acid, dimethylterephthalic acid, polyethylene terephthalate polymer, and the like, which in turn can be used to make synthetic fibers. There are three commercial techniques to recover PX, fractionation, adsorption (PAREX zeolite), and crystallization. In a preferred embodiment of the invention, combinations of these recovery techniques may used to lower capital costs. In another preferred embodiment of the invention, crystallization is used, particularly single-stage crystallization. Single-stage crystallization simply means that only one crystallization step is used on the product from the inventive process, which would be a simple and relatively inexpensive procedure. Because of the high quality product produced by the inventive process, it is expected that the PX proportion in the product from the inventive process may be 80% or more, while after one crystallization step, the proportion may be 99% or higher.

The following examples will serve to illustrate the processes and some merits of the present invention. It is to be understood that these examples are merely illustrative in nature and that the present process is not necessarily limited thereto.

EXAMPLE 1

This example illustrates that in-situ selectivation at the start-up of a xylene synthesis reaction by alkylation of toluene with syngas improves catalyst selectivity to para-xylene without loss of catalyst activity.

The catalyst used in this example contained 50 wt % of Cr and Zn mixed metal oxides and 50 wt % of MgO-modified H-ZSM-5 (SiO$_2$/Al$_2$O$_3$=25).

The Cr/Zn mixed metal oxides were prepared by co-precipitation of Cr(NO$_3$)$_3$ and Zn(NO$_3$)$_2$ with NH$_4$OH. 7.22 grams of the Cr(NO$_3$)$_3$ and 13.41 grams of the Zn(NO$_3$)$_2$ were separately dissolved in 100 ml distilled water. The two solutions were then mixed together, and NH$_4$OH was slowly added into the mixed solution with stirring until the pH value of the solution reached about 8. The precipitate was filtered, recovered, and dried at a temperature of 120° C. for 12 hours, and then calcined in air at 500° C. for 6 hours. The resultant Cr/Zn mixed metal oxides were ground into a powder.

The MgO modified H-ZSM-5 was prepared by impregnation of the zeolite with a Mg phthalate solution. The Mg phthalate was prepared by dissolving 24.0 g of Mg(OH)$_2$ in 405 g of H$_2$O, whereafter 68.8 g of phthalic acid and 60.2 g of N1l$_4$NO$_3$ were added into the Mg(OH)$_2$ solution. The mixture was heated at 80° C. under continuous stirring until a uniform solution was formed. The solution was then cooled down to room temperature. The final weight of the solution is 545.9 g.

13.7 g of the prepared solution was added to 4.6 g of H-ZSM-5 powder. The slurry was mixed well and left to sit for 30 minutes. Then the mixture was heated to about 90° C. under continuous stirring until it was dried. This sample was further dried at 120° C. for 6 hours, heated to 500° C. with a heating rate of 5° C./min, and calcined at 500° C. for 8 hours under flowing air. The resultant sample was treated with 9.8 g of the Mg phthalate solution and the same mixing, drying and calcination steps were repeated to produce the final MgO modified H-ZSM-5 catalyst.

A dual-function catalyst composition was prepared by physically mixing 2.0 grams of the Cr/Zn mixed metal oxides and 2.0 grams of the MgO modified H-ZSM-5 in a grinding mortar. The resultant catalyst composition was pelletized and screened to 8-12 mesh particles. The catalyst composition had a Diffusion Parameter, $D/r^2$, of 485 for 2,2-dimethylbutane and 1325 for 2,3-dimethylbutane when measured at a temperature of 120° C. and a 2,2-dimethylbutane relative pressure of 0.013 and a 2,3-dimethylbutane relative pressure of 0.012, respectively.

The catalyst was pretreated under He at a flow-rate of 100 ml/mm at 450° C. for 1 hour at 1 atm prior to reaction. The desired production conditions include a co-feed of syngas (CO and $H_2$) and toluene with a composition of $H_2$/CO/toluene of 1/1/0.5 (molar ratio) at 460° C. and about 30.5 atm (460 psig). The WHSV (Weight Hourly Space Velocity) was about 4 $hr^{-1}$ for toluene with respect to the catalyst. An in-situ selectivation was conducted at the start-up at the same reaction temperature using the same feed but with a composition of H2/CO/toluene of 2/1/0.25 (molar ratio) and a pressure of 300 psig. The start-up selectivation was conducted for about 40 hours before changing the reaction to normal production conditions. Table 1 shows the test results of the catalyst activity (represented by toluene conversion) and selectivity to para-xylene vs. time-on-stream, and product distribution.

As shown, the toluene conversion was stable at about 32% during the selectivation phase from 0 to 40 hours, while para-xylene selectivity increased from 67 to 77%. When the reaction conditions were changed to normal production conditions, the toluene conversion shifted to 16.3%, and para-xylene selectivity to 80.3%.

TABLE 1

|  | Time-on-steam, hr | | |
| --- | --- | --- | --- |
|  | 13.2 | 39.1 | 85.7 |
| Reaction Conditions | | | |
| Feed ($H_2$/CO/Toluene, molar) | 2/1/0.25 | 2/1/0.25 | 1/1/0.5 |
| Pressure, psig | 300 | 300 | 460 |
| Temperature, ° C. | 460 | 460 | 460 |
| Conversion, % | | | |
| Toluene | 32.4 | 31.8 | 16.3 |
| CO | 22.6 | 22.6 | 21.1 |
| $H_2$ | 9.8 | 9.6 | 18.4 |
| Hydrocarbon Products | | | |
| Xylenes wt % | 73.6 | 73.6 | 67.5 |
| Others wt % | 26.4 | 26.4 | 32.5 |
| Selectivity | | | |
| Para-Xylene in Xylenes | 73.0 | 76.9 | 80.3 |

EXAMPLE 2

This example illustrates that an in-situ selectivation at a higher temperature (e.g. 550° C.) for a short period of time during normal production is also effective to enhance para-selectivity. This example employed test conditions similar to those of Example 1. At hour 112 of the time on stream, the reaction temperature was raised from the normal production temperature of 460° C. to 550° C. for about 5 hours, and then reduced back to 460° C. There was no change in pressure, flow rate and feed of the composition. The results are shown in Table 2.

It will be seen from Table 2 that during the in-situ selectivation at 550° C., the catalyst activity increased from 11.3% to about 25%, while the para-xylene selectivity first dropped from 82% to about 68% and then increased to 74%. After the reaction temperature was changed back to 460° C., para-xylene selectivity increased to about 89.7% with toluene conversion at about 16.1%. Compared to the toluene conversion before the high-temperature in-situ selectivation, the catalyst activity increased from 11.3% to 16.1% while the para-xylene selectivity increased from 82.3% to 89.7%.

TABLE 2

|  | Time-on-steam, hr | | |
| --- | --- | --- | --- |
|  | Before Selectivation | During 5-hour Selectivation | After Selectivation |
| Reaction Conditions | | | |
| Feed ($H_2$/CO/Toluene, molar) | 1/1/0.5 | 1/1/0.5 | 1/1/0.5 |
| Pressure, psig | 460 | 460 | 460 |
| Temperature, ° C. | 460 | 550 | 460 |
| Conversion, % | | | |
| Toluene | 11.3 | 28.7 | 16.1 |
| CO | 17.9 | 25.3 | 20.6 |
| $H_2$ | 14.8 | 30.1 | 18.2 |
| Hydrocarbon Products | | | |
| Xylenes wt % | 65.5 | 60.3 | 70.0 |
| Others wt % | 34.5 | 39.7 | 30.0 |
| Selectivity | | | |
| Para-Xylene in Xylenes | 82.3 | 67.3-74.3 | 89.7 |

The Diffusion Parameter of the catalyst for 2,2- and 2,3-dimethylbutane was measured at the end of the run in Example 2 (after approximately 130 hours on stream). It was found that the Diffusion Parameter 2,2-dimethylbutane had decreased to 3 and for 2,3-dimethylbutane had decreased to 180, again when measured at a temperature of 120° C. and a 2,2-dimethylbutane relative pressure of 0.013 and a 2,3-dimethylbutane relative pressure of 0.012, respectively, thereby indicating that the in-situ selectivation had increased the diffusional resistance of the catalyst.

The invention claimed is:

1. A process for the selective production of para-xylene comprising the steps of reacting an aromatic hydrocarbon selected from toluene, benzene and mixtures thereof with a gas stream comprising carbon monoxide and hydrogen in the presence of a catalyst, said catalyst comprising: (i) a zeolite having a constraint index of from 1 to 12; (ii) and at least one metal selected from zinc, copper, chromium, cadmium, palladium, ruthenium, and magnesium; said catalyst further characterized by said at least one metal present in the amount of 0.1wt % to 50wt %, based on the weight of the total catalyst; wherein said process includes a catalyst selectivation phase and a para-xylene production phase and wherein:
 (a) said catalyst selectivation phase includes the step of contacting said aromatic hydrocarbon and said gas stream with said catalyst under a first set of conditions effective to decrease the diffusivity of said catalyst and increase the para-selectivity of said catalyst, and
 (b) said para-xylene production phase includes the step of contacting said aromatic hydrocarbon and said gas stream with said catalyst under a second set of conditions different from said first set of conditions and effective to selectively produce para-xylene;
 with the proviso that said first set of conditions and said second set of conditions differ at least in one of temperature, molar concentration and/or feed rate of at least one of said aromatic hydrocarbon, carbon monoxide and hydrogen, and wherein step (a) does not involve the addition of a selectivating agent different from said aromatic hydrocarbon and said gas stream.

2. The process of claim 1, wherein step (b) comprises a treatment with carbon monoxide at conditions effective to increase the diffusional resistance of the catalyst such that the catalyst has a Diffusion Parameter, $D/r^2$, for 2,2-dimethylbutane of less than 100, when measured at a temperature of 120° C. and a 2,2-dimethylbutane relative pressure of 0.013, said process further comprising, after said treatment at least one step of determining that the diffusional resistance has increased sufficiently to meet said $D/r^2$ limitation.

3. The process of claim 2 wherein the catalyst has a Diffusion Parameter, $D/r^2$, for 2,2-dimethylbutane of less than 5, when measured at a temperature of 120° C. and a 2,2-dimethylbutane relative pressure of 0.013.

4. The process of claim 2 wherein the catalyst has a Diffusion Parameter, $D/r^2$, for 2,3-dimethylbutane of less than 1000, when measured at a temperature of 120° C. and a 2,3-dimethylbutane relative pressure at 120° C. of 0.012.

5. The process of claim 2 wherein the catalyst has a Diffusion Parameter, $D/r^2$, for 2,3-dimethylbutane of less than 600, when measured at a temperature of 120° C. and a 2,3-dimethylbutane relative pressure at 120° C. of 0.012.

6. The process of claim 2 wherein said reacting step is effected under conditions including a temperature of about 100 to about 700° C., a pressure of about 1 to about 300 atm. and a flow rate for the hydrocarbon feed of about 0.01 to about $100^{-1}$ LHSV on a liquid feed basis.

7. The process of claim 2 wherein said reacting step and the selectivation phase are effected under conditions including a temperature of about 200 to about 600° C., a pressure of about 1 to about 200 atm. and a flow rate for the hydrocarbon feed of about 1 to about $50^{-1}$ LHSV on a liquid feed basis, and wherein the mole ratio of $H_2$/CO/aromatic compound is about 0.01-10/0.01-10/0.01-10.

8. The process according to claim 2, wherein the selectivation phase occurs before the production phase.

9. The process according to claim 2, wherein the selectivation phase interrupts the production phase, which resumes once the selectivation phase is completed.

10. The process according to claim 2, wherein the temperature of the selectivation phase is greater than that of the production phase.

11. The process of claim 1, wherein said catalyst further includes an inorganic oxide.

12. The process of claim 1, wherein (i) includes HZSM-5 and (ii) includes zinc, copper, and mixtures thereof.

* * * * *